US008571629B2

(12) United States Patent
Faro et al.

(10) Patent No.: US 8,571,629 B2
(45) Date of Patent: Oct. 29, 2013

(54) DETECTION OF DECEPTION AND TRUTH-TELLING USING FMRI OF THE BRAIN

(75) Inventors: Scott H. Faro, Haddonfield, NJ (US); Feroze B. Mohamed, Philadelphia, PA (US); Nathan J. Gordon, Philadelphia, PA (US); Steven M. Platek, Lawrenceville, GA (US)

(73) Assignee: Truth Test Technologies, LLC, Philadelphia, PA (US)

( * ) Notice: Subject to any disclaimer, the term of this patent is extended or adjusted under 35 U.S.C. 154(b) by 260 days.

(21) Appl. No.: 12/514,504

(22) PCT Filed: Nov. 13, 2007

(86) PCT No.: PCT/US2007/023950
§ 371 (c)(1),
(2), (4) Date: Dec. 17, 2009

(87) PCT Pub. No.: WO2008/063527
PCT Pub. Date: May 29, 2008

(65) Prior Publication Data
US 2010/0099975 A1    Apr. 22, 2010

Related U.S. Application Data

(60) Provisional application No. 60/858,608, filed on Nov. 13, 2006.

(51) Int. Cl.
*A61B 5/05* (2006.01)
(52) U.S. Cl.
USPC ............... 600/410; 607/2; 607/45; 607/115; 600/9; 600/15; 600/300; 600/411; 600/413; 600/544; 600/407; 374/45

(58) Field of Classification Search
USPC ............... 600/9–15, 300, 410, 411, 413, 544, 600/545; 607/2, 45, 115; 374/45
See application file for complete search history.

(56) References Cited

U.S. PATENT DOCUMENTS

| 4,520,404 A | 5/1985 | Von Kohorn |
| 4,704,725 A | 11/1987 | Harvey et al. |

(Continued)

FOREIGN PATENT DOCUMENTS

WO    03049605 A2    6/2003

OTHER PUBLICATIONS

International Search Report for Application No. PCT/US07/23950 dated Jun. 24, 2008.

*Primary Examiner* — Unsu Jung
*Assistant Examiner* — Joseph M Santos
(74) *Attorney, Agent, or Firm* — Lerner, David, Littenberg, Krumholz & Mentlik, LLP

(57) ABSTRACT

Methods for deriving an indication of truth or deception are disclosed. Some methods include (a) monitoring the activation of a plurality of regions of a subject's brain, while the subject responds to questions and (b) measuring one or more physiological parameters while the subject responds to questions and combining the results of (a) and (b) to form a composite evaluation indicative of truth or deception in the subject's response. Another method further includes (c) measuring one or more behavioral components while the subject responds to questions and then combining the results of (a), (b), and (c) to form a composite evaluation indicative of truth or deception in the subject's response. Methods for scoring, weighting, and combining the measurements for (a), (b), and (c), and combinations thereof, are also disclosed.

20 Claims, 7 Drawing Sheets

(56) References Cited

U.S. PATENT DOCUMENTS

| | | | |
|---|---|---|---|
| 4,930,158 A | 5/1990 | Vogel | |
| 4,945,563 A | 7/1990 | Horton et al. | |
| 5,054,064 A | 10/1991 | Walker et al. | |
| 5,400,402 A | 3/1995 | Garfinkle | |
| 5,796,828 A | 8/1998 | Tsukamoto et al. | |
| 6,061,319 A | 5/2000 | Fujiki | |
| 6,754,524 B2 | 6/2004 | Johnson, Jr. | |
| 2002/0058867 A1 | 5/2002 | Breiter et al. | |
| 2003/0032870 A1 | 2/2003 | Farwell | |
| 2003/0120140 A1 | 6/2003 | Bango | |
| 2004/0215082 A1 | 10/2004 | Chance | |
| 2005/0119547 A1* | 6/2005 | Shastri et al. | 600/407 |
| 2005/0143629 A1 | 6/2005 | Farwell | |
| 2005/0154290 A1 | 7/2005 | Langleben | |
| 2005/0159671 A1 | 7/2005 | Sneddon | |
| 2005/0228291 A1 | 10/2005 | Chance | |
| 2006/0036152 A1 | 2/2006 | Kozel | |
| 2006/0036153 A1 | 2/2006 | Laken | |
| 2007/0191704 A1* | 8/2007 | DeCharms | 600/411 |

\* cited by examiner

Diagram shows the hypothetical model of deception. GSR = guilty subject response.

Questioning strategy for guilty subjects (GS).

| BRAIN LOBE | GYRUS | AREA | BRAIN LOBE | GYRUS | AREA |
|---|---|---|---|---|---|
| Frontal Lobe | | | Occipital Lobe | | |
| | Middle frontal gyrus | L | | Middle occipital gyrus | L |
| | Middle frontal gyrus | R | | Middle occipital gyrus | R |
| | Medial frontal gyrus | L | | Inferior occipital gyrus | L |
| | Medial frontal gyrus | R | | Inferior occipital gyrus | R |
| | Superior frontal gyrus | L | | Lingual gyrus | L |
| | Superior frontal gyrus | R | | Lingual gyrus | R |
| | Inferior frontal gyrus | L | | Subgyral | L |
| | Inferior frontal gyrus | R | | Subgyral | R |
| | Subgyral gyrus | L | | Fusiform gyrus | L |
| | Subgyral gyrus | R | | Fusiform gyrus | R |
| | Precentral gyrus | L | | Cuneus | L |
| | Precentral gyrus | R | | Cuneus | R |
| | Cingulate gyrus | L | | Inferior temporal gyrus | L |
| | Cingulate gyrus | R | | Inferior temporal gyrus | R |
| | Paracentral lobule | L | | Precuneus | L |
| | Paracentral lobule | R | | Precuneus | R |
| Temporal Lobe | | | Sublobar Area | | |
| | Superior temporal gyrus | L | | Corpus callosum | L |
| | Superior temporal gyrus | R | | Corpus callosum | Interlobar |
| | Middle temporal gyrus | L | | Insula | L |
| | Middle temporal gyrus | R | | Insula | R |
| | Fusiform gyrus | L | | Extranuclear | L |
| | Fusiform gyrus | R | | Extranuclear | R |
| | Subgyral | L | | | |
| | Inferior temporal gyrus | L | | | |
| | Inferior temporal gyrus | R | | | |

Fig. 4A

| BRAIN LOBE | GYRUS | AREA | BRAIN LOBE | GYRUS | AREA | |
|---|---|---|---|---|---|---|
| Limbic Lobe | | | Cerebellum | | | |
| | Cingulate gyrus | L | | Posterior lobe | | |
| | Cingulate gyrus | R | | | Inferior semilunar lobule | |
| | Posterior cingulate gyrus | L | | | Inferior semilunar lobule | L |
| | Posterior cingulate gyrus | R | | | Declive | R |
| | Anterior cingulate gyrus | L | | | Declive | L |
| | Anterior cingulate gyrus | R | | | Tuber | R |
| | Uncus | L | | | Tuber | L |
| | Uncus | R | | | Cerebellar tonsil | R |
| | Parahippocampal | L | | | Cerebellar tonsil | L |
| | | | | | Pyramis | R |
| | Parahippocampal | R | | | Pyramis | L |
| | | | | | Uvula | R |
| Parietal Lobe | | | | | Uvula | L |
| | Post-central gyrus | L | | | | R |
| | Post-central gyrus | R | Anterior Lobe | Culmen | | |
| | Precuneus | L | | Culmen | L | |
| | Precuneus | R | Sublobar | | | R |
| | Supramarginal gyrus | L | | | | |
| | Supramarginal gyrus | R | Thalamus | VL nucleus | | |
| | Angular gyrus | L | | VL nucleus | L | |
| | Angular gyrus | R | | | | R |
| | Inferior parietal gyrus | L | | | | |
| | Inferior parietal gyrus | R | | | | |
| | Superior parietal lobule | L | | | | |
| | Superior parietal lobule | R | | | | |
| Brain Stem | | | | | | |
| | Medulla | L | | | | |
| | Medulla | R | | | | |

Overall areas activated during questioning strategies for guilty and non-guilty subjects.

Fig. 4B

| Subject Initials | Ground Zero | ASIT Score | ASIT Determination | fMRI Score | fMRI Determination | Total Score | Combined Determination |
|---|---|---|---|---|---|---|---|
| PD | DI | -39 | DI | -71 | DI | -110 | DI |
| KS | DI | -40 | DI | -95 | DI | -135 | DI |
| JR | NDI | +26 | NDI | -6.75 | INC | +19.25 | NDI |
| JB | NDI | +5 | INC | 21.6 | NDI | +26.6 | NDI |
| LH | NDI | +36 | NDI | 0 | INC | +36 | NDI |
| MC | DI | -24 | DI | -63.45 | DI | -87.45 | DI |
| NM | DI | -58 | DI | 0 | INC | -58 | DI |
| SM | DI | -23 | DI | -108 | DI | -131 | DI |
| BB | DI | -32 | DI | -139.05 | DI | -171.05 | DI |
| SP | NDI | +54 | NDI | +28.35 | NDI | +82.35 | NDI |
| SK | NDI | +16 | NDI | +76.95 | NDI | +95.95 | NDI |

The results from combining the fMRI score with the polygraph score using the ASIT algorithm.

Fig. 5

| Subject Initials | Ground Zero | OSS | OSS Determination | fMRI Score | fMRI Determination | Total Score | Combined Determination |
|---|---|---|---|---|---|---|---|
| PD | DI | -22 | DI | -71 | DI | -93 | DI |
| KS | DI | -39 | DI | -95 | DI | -134 | DI |
| JR | NDI | +20 | NDI | -6.75 | INC | +13.25 | INC |
| JB | NDI | +8 | INC | 21.6 | NDI | +29.6 | NDI |
| LH | NDI | +44 | NDI | 0 | INC | +44 | NDI |
| MC | DI | 0 | INC | -63.45 | DI | -63.25 | DI |
| NM | DI | -65 | DI | 0 | INC | -65 | DI |
| SM | DI | -17 | DI | -108 | DI | -125 | DI |
| BB | DI | -30 | DI | -139.05 | DI | -160.05 | DI |
| SP | NDI | +26 | NDI | +28.35 | NDI | +54.35 | NDI |
| SK | NDI | +3 | INC | +76.95 | NDI | +79.95 | NDI |

The results from combining the fMRI score with the polygraph score using the OSS algorithm.

Fig. 6

| No. | Type | Question |
|---|---|---|
| 1. | Irrelevant | Is your first name _____? |
| 2. | Outside issue | Do you understand that I will only ask the questions I reviewed? |
| 3. | Weak relevant | Do you intend to deliberately lie to any test question? |
| 4. | Irrelevant | Were you born in _____? |
| 5. | Comparison | During the first (-2 years from current age), did you ever lie to make yourself look better? |
| 6. | Relevant | Today, did you fire that gun? |
| 7. | Irrelevant | Is your last name _____? |
| 8. | Comparison | In your entire life did you ever cheat? |
| 9. | Relevant | Regarding that gun, did you fire it today? |
| 10. | Irrelevant | Is today Sunday? |
| 11. | Comparison | During the first (-2 years from current age), did you ever take credit for something you did not do? |
| 12. | Relevant | Did you lie about whether you fired that gun today? |
| 13. | Countermeasure | Did you deliberately do anything to try and beat this test? |

The questioning format used during the Integrated Zone Comparison Technique (IZCT) polygraph technique.

Fig. 7

DETECTION OF DECEPTION AND TRUTH-TELLING USING FMRI OF THE BRAIN

CROSS-REFERENCE TO RELATED APPLICATIONS

This application claims the benefit of the filing date of U.S. Provisional Patent Application No. 60/858,608 filed Nov. 13, 2006, the disclosure of which is hereby incorporated herein by reference.

BACKGROUND OF THE INVENTION

Determining whether an individual is telling the truth or telling a lie has been a goal of humankind for centuries. Early methods of lie detection—as well as some modern techniques—rely on observations of proposed nonverbal indicators of deception, such as increased perspiration, changing body positions, or subtle facial expressions. However, there has been an effort to develop and use technology (i.e., the standard polygraph and infrared thermal imaging to aid in the identification of deception by measuring changes in sympathetic nervous system responses.

Of several techniques that are currently used and several others that are being developed to aid in the detection of deception, the standard polygraph examination is the most reliable (reliability, 80%-90%) and widely used. Although the polygraph test has become the most common method used to detect deception, it has several drawbacks. Functional magnetic resonance (MR) imaging based on blood oxygen level-dependent (BOLD) imaging is a method that is used to measure indirect responses that are tightly coupled with neuronal activity, and it is used to map human brain functions. This technique may enable accurate mapping of the regions of the brain that are involved in higher cortical functions, including cognitive processes such as deception and truth telling. Results of several functional MR imaging studies have shown the prefrontal cortices, parietal lobes, and anterior cingulate are activated during judgment, manipulation of information, and planning of response, including inhibition. None of these studies, however, used standard polygraph techniques or innovations from that field of expertise.

Other studies have been conducted that examine brain activity during deception and truth telling by using functional MR imaging and compare these results with the results of a standard polygraph examination [Mohamed, F. B., Faro, S. H., Gordon, N. J., Platek, S. M., Ahmad, H. A, Williams, J. M., *Neuroradiology* 238(2):679-688 (2006)].

SUMMARY OF THE INVENTION

One aspect of the present invention provides methods for deriving an indication of truth or deception in a subject. The method according to this aspect of the invention desirably includes (a) monitoring the activation of a plurality of regions of a subject's brain while the subject responds to questions including relevant questions and (b) measuring one or more physiological parameters while the subject responds to questions including relevant questions; and combining the results of steps (a) and (b) to form a composite evaluation indicative of truth or deception in the subject's response to the relevant questions.

In some embodiments, the subject's brain activation is monitored while responding to both control and relevant questions. In these embodiments, the step of monitoring the activation of the subject's brain may include comparing an indicium of activity for each of the monitored regions during the response period. In these methods, the subject's response to the control questions can include known lies and known truths.

The combining step may include applying a weighting factor to the indicium of response for each monitored region of the subject's brain. The weighting factor for each region desirably is related to the probability that the activation of such region indicates deception. Thus, known regions activated that are associated with truthfulness may be assigned a first sign (e.g., "+") whereas those regions activated associated with deceptiveness may be assigned an opposite sign (e.g., "−"). The step of applying a weighting factor to a known region associated with truth or deception may include multiplying an indicium of activation by the weighting factor for such region. The weighting factor may be determined by monitoring the activation of a plurality of regions of a plurality of subjects while the subjects respond to control questions.

The step of monitoring activation of a plurality of regions of a subject's brain may be performed by a technique selected from the group consisting of functional magnetic resonance imaging (fMRI), magnetoencephalography (MEG), electroencephalography (EEG), positron emission tomography (PET), photon emission, single photon emission tomography (SPECT), functional infrared, functional near infrared (fNIR), computerized tomography, diffuse optical imaging (DOI), ultrasound, X-ray computer tomography, optical imaging, nuclear particle emission, event-related potential (ERP), ERP/EEG, and combinations thereof. Other monitoring techniques may be used.

The step of measuring one or more physiological parameters desirably includes measuring one or more parameters, and most preferably a plurality of parameters, selected from the group consisting of respiratory rate, respiratory volume, heart rate, blood pressure, blood volume, electrodermal activity, pupil size, and skin temperature. The step of measuring one or more parameters may include measuring changes in the one or more parameters while the subject responds to control and relevant questions. In a further embodiment, a degree of reactivity may be quantified based on a subject's response and recorded as a real number.

The combining step may include calculating a composite activation score based on the degrees of activation of all of the plurality of brain regions, calculating a composite physiological score based on measurements of all of a plurality of physiological parameters, and combining the activation score with the physiological score.

The step of calculating a composite physiological score optionally may be performed using at least one polygraph scoring algorithm such as PolyScore®, OSS, ASIT Poly Suite and combinations thereof.

The steps of monitoring activation of the subject's brain and measuring the physiological parameters while the subject responds to questions are conducted simultaneously. In yet other embodiments, the steps can be conducted at different times.

Another aspect of the present invention provides additional methods of deriving an indication of truth or deception. Methods according to this aspect of the invention desirably include (a) monitoring activation of a plurality of regions of a subject's brain while the subject responds to questions including relevant questions; (b) measuring one or more physiological parameters while the subject responds to questions including relevant questions; (c) measuring one or more behavioral components while the subject responds to questions including relevant questions; and combining the results of steps (a) and (b) and (c) to form a composite evaluation indicative of truth or deception in the subject's response to the relevant questions. The steps of measuring activation, measuring physiological parameters and/or behavioral components may be performed generally as discussed above in connection with the preceding aspect of the invention. In some embodiments, the step of measuring the behavioral components may include, for example, measuring spoken verbal behavior, non-verbal behavior, and written behavior.

The step of measuring one or more physiological parameters desirably includes measuring a plurality of physiological parameters and the step of measuring one or more behavioral components desirably includes measuring a plurality of behavioral components. The combining step may include calculating a composite activation score based on the degrees of activation of all of the brain regions, calculating a composite physiological score based on measurements of the physiological parameters, calculating a composite behavioral score based on measurements of the behavioral components, and combining the activation score with the physiological score and with the behavioral score.

Yet another aspect of the present invention provides a method for deriving an indication of truth or deception by (a) monitoring activation of a plurality of regions of a subject's brain while the subject responds to questions including relevant questions; (b) measuring one or more behavioral components while the subject responds to questions including relevant questions; and combining the results of steps (a) and (b) to form a composite evaluation indicative of truth or deception in the subject's response to the relevant questions.

In another aspect, the invention provides an alternative method for deriving an indication of truth or deception. The method includes (a) measuring one or more physiological parameters while the subject responds to questions including relevant questions; and (b) measuring one or more behavioral components while the subject responds to questions including relevant questions; and combining the results of steps (a) and (b) to form a composite evaluation indicative of truth or deception in the subject's response to the relevant questions.

BRIEF DESCRIPTION OF THE DRAWINGS

FIGS. 4A and 4B illustrate the overall areas activated during questioning strategies for guilty and non-guilty subjects.

FIG. 5 illustrates the results of combining the fMRI score with the polygraph score using the ASIT algorithm.

FIG. 6 illustrates the results of combining the fMRI score with the polygraph score using the objective scoring system (OSS).

FIG. 7 illustrates the questioning format used during the Integrated Zone Comparison Technique (IZCT) polygraph technique.

DETAILED DESCRIPTION

Figure 1:
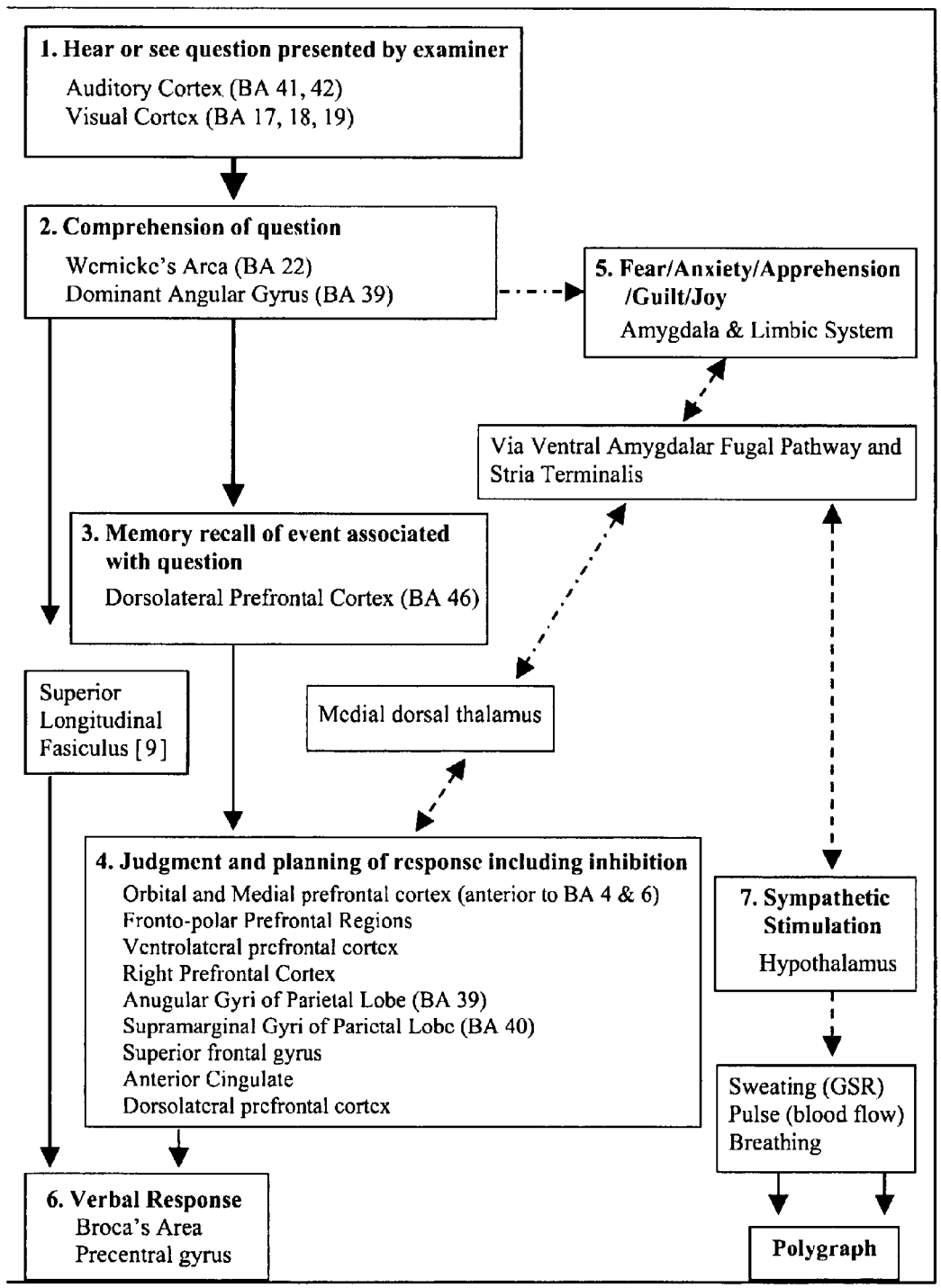
FIG. 1 depicts a flowchart illustrating a hypothetical model of deception.

Although the present invention is not limited by any operational mechanism or theory of operation, it is noted that: (1) when an individual is being deceptive they become measurably nervous about lying and that brain imaging and scanning devices can detect quantifiable differences and patterns in regional brain activity that are indicative or truth-telling or deception; (2) polygraph devices can detect measurable responses in individuals who become measurably nervous about their lying; and (3) measurements of externally measurable behavioral components can be quantified to indicate a likelihood of truth-telling or deception.

The process of producing a lie or truthful response begins with hearing or seeing the question, understanding it, and then recalling the event or fact that relates to the question. The perception of the question by means of hearing or vision activates the corresponding auditory cortex (Brodmann areas (BAs) 41 and 42) or visual cortex (BAs 17, 18, and 19). This is followed by receptive language comprehension, which has been linked to activation in the Wernicke area (BA 22), which comprises the posterior portion of the superior temporal gyrus, and the dominant angular cortex (BA 39). Once the question posed to the person is understood, he or she may attempt to recall the event associated with the question. Although the role of the frontal lobes in recall of memory is unclear, areas in the prefrontal cortex are likely to be involved in moderating memory. The amygdala is an area of the brain associated with emotions such as fear and anxiety. Functional MR imaging studies have shown that recall of an event that is associated with anxiety stimulates the amygdala. It should not be misunderstood that activation of the amygdala is representative of inhibition or deception, as one can recall and speak truthfully of an event that involves anxiety.

The polygraph is used to measure the output of the limbic system, including the amygdala, which regulates functions of the sympathetic nervous system, such as heart rate, respiratory rate, and electrodermal response. The limbic system may be activated in situations of anxiety or fear, regardless of the nature of the responses of a subject.

After recall of the event of importance, the subject must plan a response consistent with truth or deception. If a person wishes to answer a question truthfully, the person will plan and construct a truthful response. If a person wishes to produce a deceptive response, it is hypothesized that either an additional area of the brain is marshaled to produce such a response or, perhaps, a different activation of the same area is needed to construct the deceptive response. In producing a deceptive response, inhibition or concealment of the truth is obviously a key aspect of the construction. It is this step in the process of deception that has been the focus of intense study with functional MR imaging, since this is the unique cognitive function in the process of lying.

There is some consensus among investigators that the prefrontal cortex is an area involved in planning a deceptive response and inhibiting the truth. Some functional MR imaging studies of deception demonstrated activation of the anterior cingulated cortex and areas of the right hemisphere. The final component of producing a deceptive or truthful statement involves motor response. These responses may include a truthful or deceptive utterance, or simply pushing a "yes" or "no" response key in the imager. Such a response involves the use of the motor system in the frontal lobe.

On the basis of the foregoing information, a working neurologic model of deception to better illustrate the cognitive complexities involved in formulating a lie is provided (FIG. 1). The illustration takes into account data that are focused on the neural components of deception and data that pertain to neural substrates associated with processes such as inhibition and reward circuitry. It also shows the chain of events involved in conventional polygraph testing.

All references to techniques disclosed herein, shall refer to the techniques as commonly understood in the art and include substitutions, variations, and later-developed techniques that would be apparent to one of ordinary skill in the relevant art.

A. Methods of Monitoring and Scoring Brain Activation.

In some embodiments of the present invention, a plurality of regions of a subject's brain is monitored while the subject responds to questions, including relevant questions. In this respect, the subject is asked a series of control questions in combination with relevant questions while being monitored by a brain imaging or scanning or measuring device. Here, the indicium of activity in each region during the subject's response to a relevant question can be compared with the same indicium during the response to a control question.

In some embodiments, the indicium of activity is represented as a binary indicator, i.e., a first value may be indicative of activation and a second value may be indicative of inactivation. In a preferred embodiment applying the binary scoring method, a "1" score is indicative of activation and a "0" score is indicative of inactivation. In other embodiments, the indicium of activity in a brain region is scored as a degree of activation. Here, the degree of activation can be scored as a non-binary number, i.e., a real number value or integer. The degree of activation during response to a relevant question can be evaluated by comparing the measured level of activation during response to the relevant question relative to the level of activation of the same area measured during response to control questions. For example, in applying this scoring technique, a "1" score may be indicative of a small amount of activity in a monitored region and a "6" score may be indicative of a large response.

A weighting factor may be applied to the indicium of response for each of the monitored regions of the subject's brain. The weighting factor is related to the probability that the activation of such a region indicates deception. Thus, regions of the brain for which activation is associated with truthfulness are assigned a weighting factor having first sign (e.g., "+"). Regions that which are commonly activated during deception are assigned an opposite sign (e.g., "−"). The weighting factor associated with each region may have equal magnitudes, i.e., either a +1 for each region associated with truthfulness and a −1 for each region associated with deception. Most preferably, however, the weighting factors have different magnitudes so that the magnitude of the weighting factor for each region of the brain varies directly with the strength of the association between activation of such region and truthfulness or deception. Thus, a region of the brain for which activation is very strongly associated with deception may have a weighting factor of −5, whereas a region only weakly associated with deception may have a weighting factor of −1, and so on.

The step of combining a weighting factor with an indicium of activation for a particular region may include multiplying the indicium of activation by the weighting factor for such region to yield a score for the individual region. The scores for the individual regions can be added to yield the score for activation as a whole. For example, a −6 score can be indicative of a large response in a region of the brain associated with lying.

The weighting factors can be determined by monitoring the activation of a plurality of regions of a plurality of subjects while the subjects respond to control questions. For example, control questions for which the answer is known to the investigator can be posed to a group of control subjects. The responses of the various regions within the brains of the control subjects can be monitored, and the association between activation and truthfulness or deception for each region can be derived from these responses. The control group subjects need not be the same individuals as the real subjects who are to be examined for truthfulness or deception as to relevant questions.

The quantitative determination of a brain activation score may be generated from a modified control test questioning technique or other questioning techniques, including for example, a truth-only testing technique, a lie-only testing technique, or a mixed truth and lie testing technique.

To reduce variability between individuals within the control group and the real subject, the individuals within the group can be matched to each other and to the real subject based on various criteria. For example, individuals can be matched for age, sex, race, ethnicity, handedness, language skills (e.g., native language), health, socioeconomic status, and personality profile. The degree of matching is entirely within the discretion of the practitioner. Based upon a variety of reports in the field of brain imaging, however, it is generally believed that matching for sex, age, medical/psychiatric condition and handedness is most significant. It is also possible to derive the weighting factors by examining the response of the real subjects to control questions with known answers. Conversely, published values for weighting factors, such as the weighting factors used in Example 1, below, can be used.

Questions may be asked by any means which are effective to communicate with the subject. For example, and without limitation, an investigator can ask questions orally, questions can be presented on printed materials, an audio recording of questions can be played, or questions can be presented on a video screen. In addition, as noted above, a general question (e.g., "Do you recognize the object in any of the following pictures?") or general instruction (e.g., "Press the button if you recognize the object in any of the following pictures.") can be asked, optionally, followed by a series of stimuli (e.g., aural, visual, or otherwise) to which the question or instruction is applied.

In some embodiments, the nature of the brain activity measuring device may favor one format or another for asking questions. For example, in an MRI device, the subject's head is enclosed within the device and the device generates significant levels of noise. Therefore, for embodiments employing MRI devices, it may be preferred to ask questions visually using, for example, video goggles or a video screen, or to present questions aurally using, for example, MR-compatible ear plugs or head phones (as employed in Example 1 below).

When using a brain imaging device, in order to limit the brain regions involved in a response, to isolate activity which is not involved in deception, as well as to reduce variability between individuals, questions may be chosen such that the number of possible responses is limited. For example, questions with "yes" or "no" answers, or multiple choice questions, can be used. Such questions avoid the mental activity associated with formulating more complicated verbal or written responses.

Devices and methods for measuring brain activity are suitable for use in the present invention. These include, without limitation, fMRI, magnetoencephalography (MEG), electroencephalography (EEG), positron emission tomography (PET), photon emission, single photon emission tomography (SPECT), functional infrared, functional near infrared (fNIR), computerized tomography, diffuse optical imaging (DOI), ultrasound, X-ray computer tomography, optical imaging, nuclear particle emission, event-related potential (ERP), ERP/EEG, and combinations thereof. Such methods are inclusive of BOLD, non-BOLD, diffuse optical tomography (DOT), quantitative electroencephalography (qEEG), and optical tomography. Other techniques may be used. In addition, it is expected that new devices will be developed in the future to measure brain activity, and that some will be useful in the methods of the present invention.

Thus, the brain region(s) that can be monitored in accordance in any of the forgoing embodiments can include the prefrontal cortex, limbic cortex, anterior cruciate, temporal cortex, parietal cortex, caudate, hypothalamus and cerebellum. In some embodiments, the brain regions can be chosen from orbitofrontal cortex, anterior cingulate cortex, prefrontal cortex, middle temporal cortex, insula, cuneus, post-central gyrus, pre-central gyrus, superior temporal gyrus and cerebellum. In certain embodiments, the brain region(s) can be chosen from the right anterior cingulate cortex, right inferior frontal cortex, right orbitofrontal cortex, left middle temporal cortex and right middle frontal cortex.

In specific embodiments, the brain region(s) can be selected from a particular region associated with deception and can include the frontal lobe (left medial, left inferior, and bilateral precentral gyri) (Brodmann areas [BAs] 9, 10, and 6), temporal lobe (right hippocampus and right middle temporal gyrus) (BA 19), parietal lobe (bilateral precuneus and right inferior parietal lobule) (BA 40), occipital lobe (left lingual gyrus) (BA 18), and anterior and posterior cingulate, right fusiform gyrus, and right sublobar insula and thalamus regions [Mohamed, F. B., et al. supra].

In other specific embodiments, the brain region(s) can be selected from a particular region associated with truthfulness and can include the frontal lobe (right precentral, left subcallosal lentiform nucleus) (BAs 46 and 10), temporal lobe (left inferior temporal gyrus) (BA 20), parietal lobe (right precuneus, left inferior parietal lobule), and posterior cingulate gyrus [Mohamed, F. B., et al. supra].

In embodiments in which the subject has reversed left-right brain symmetry relative to the majority of the population, the terms "right" and "left" are reversed for the brain region(s).

Various types of MRI devices can be employed in the methods of the invention, and a number of parameters relating to an MRI scan can be varied. For example, MRI devices generating magnetic fields varying from 0.5 to 7.0 Tesla (T) are commercially available, although magnetic fields of 1.5-4.0 T are more commonly used for fMRI. MRI devices with stronger magnetic fields are generally more sensitive and can, therefore, provide higher resolution images. MRI images of the brain are typically acquired in a series of 10-40 co-planar slices, in which each slice is 1-8 mm in thickness, but these values can vary depending on the area of interest and the specific question being addressed. An entire image of the brain is typically obtained in 1-5 seconds, but certain situations can require a shorter or longer duration to acquire a complete picture of the brain.

Since fMRI uses an MRI device, the standard preparations for an MRI procedure are necessary. Because of the strong magnetic fields generated by MRI devices, subjects with metal implants (other than dental fillings), shrapnel, or irremovable medical devices (e.g., pacemakers, fixed hearing aids, artificial valves) should not be examined in an MRI device. Thus, any devices for use in conjunction with the imaging procedures of the present invention should be compatible for use in the environment created by the device.

Methods or devices for statistically analyzing changes in brain activity are inclusive of fMRI time series analysis and image data mining methods and devices associated therewith. [Shekar, S., Zhang, P., Huang, Y., and Vatsavai, R., Trends in Spatial Data Mining (2004), published in Kargupta, H., Joshi, A., Sivakumar, K., and Yesha, Y., eds., Data Mining: Next Generation Challenges and Future Directions, Ch. 3, MIT Press, (2004)]. For some brain activity measuring devices, computer software packages are commercially available which are specifically adapted to analyze the data. For example, SPECT, PET or MRI data can be analyzed using the Dot or EMMA (Extensible MATLAB Medical image Analysis) packages which are both freely available from the MNI, or the SPM software package which is freely available from the Functional Imaging Laboratory of the Wellcome Department of Imaging Neuroscience at the University College of London, UK. The EMMA and SPM software are based upon the MATLAB® programming language (MathWorks, Inc., Natick, Mass.), with additional routines in the C programming language. An SPM module is incorporated into the commercially available MEDx software (Medical Numerics, Inc., Sterling, Va.). FSL, AFNI, and BrainVoyager, as well as any other post-processing software program adapted to analyze brain imaging data, are also prescribed. Image post processing techniques for clustering the brain data such as dynamic recursive partitioning (DRP) as well as other data mining techniques for classification of the brain data from individual subjects may be employed. In addition, all possible permutations of statistical analysis (e.g., statistically emphasizing relevant questions compared to control and vice versa with all testing techniques) may be employed.

B. Methods of Measuring and Scoring Physiological Parameters.

In some embodiments, one or more physiological parameters are measured while the subject responds to questions, including relevant questions. In this respect, the physiological parameter(s) can be measured during the subject's response to a relevant question and compared with the subject's response to a control question. The step of measuring the physiological parameter(s) can include the step of quantifying a degree of reactivity in response to relevant and control questions. In some embodiments, the degree of reactivity can be represented by a real number. For example, a measurement during a response to a relevant question may be assigned a "6", indicative of a strong reaction relative to a measured response to the control question(s).

In some embodiments, the subject's responses to be measured may include known truths and known lies. However, it is not necessary that the investigator know prior to questioning a subject that a subject's response to a relevant question is truthful or deceptive.

Methods and devices for measuring physiological parameters are suitable for use in the present invention. In preferred embodiments, the physiological parameter(s) to be measured include, for example, respiratory rate, respiratory volume, heart rate, blood pressure, blood volume, electrodermal activity (e.g., galvanic skin conductance), pupil size, and skin temperature.

In some embodiments, an electrophysiological response to an internal or external stimulus may be measured as a physiological parameter. Electroencephalography (EEG), which measures the electrical activity of the brain by recordings from electrodes placed on the scalp or, in special cases, subdurally or in the cerebral cortex, may be employed to measure such a physiological parameter. Thus, in some embodiments, measuring a physiological parameter may include a method for monitoring brain activation, as described herein.

In another embodiment, pupilometry, which measures the dilation and contraction of the pupil relative to a stimulus or emotion being studied, may be employed to measure a physiological parameter. Pupil size is mainly controlled by the action of parasympathetic and sympathetic nerves. Thus, measurements of pupil size during a response to a stimulus may be indicative of truthful or deceptive behavior.

In some embodiments, multiple physiological parameters are measured and scored using an algorithm. Acceptable algorithms include, for example, PolyScore, OSS, ASIT Poly Suite and combinations thereof. Other acceptable algorithms that may be combined with any of the above or employed alone include, for example, QuESt Polygraph Software and Identifi Polygraph Software (available from Lafayette Instrument Company).

In some of the foregoing embodiments, measurements of one or a plurality of physiological parameters may be measured by polygraph. A polygraph is an instrument that simultaneously records changes in physiological processes such as heartbeat, blood pressure, respiration and electrical resistance (galvanic skin conductance or GSC).

The underlying theory of the polygraph is based on the principle that when people lie they also get measurably nervous about lying. For example, the heartbeat increases, blood pressure goes up, breathing rhythms change, perspiration increases, etc. A baseline for these physiological characteristics can be established by asking the subject questions whose answers the investigator may know. Deviation from the baseline for truthfulness is taken as sign of lying.

Preferably, an experienced polygraph examiner is employed to administer and score the exam. In some embodiments multiple physiological parameters are recorded (e.g., rate and depth of respiration can be recorded by two different pneumographs-one secured around the chest and one around the abdomen of the subject, cardiovascular activity may be measured and recorded using a blood-pressure cuff placed around the bicep of the subject, and perspiration levels (galvanic skin conductance) can be measured with electrodes attached to the index and forefinger of the subject). A suitable device for measuring multiple physiological parameters is the LX-4000 polygraph instrument. Other polygraph and measuring devices are also acceptable. In some embodiments, software packages (e.g., software developed by Layfayette Instrument Company; Layfayette, Ind.) can be employed to digitally record and display the responses on a computer for further analysis. In certain embodiments, the results of data may be analyzed by any suitable scoring method including PolyScore 5.5® [Matté, J. A., *Forensic psychophysiology; using the polygraph*. Williamsville, N.Y.: J.A.M. Publications (1996)], developed by Johns Hopkins University Applied Science Laboratory; Objective Scoring System (OSS) [Krapohl, D., McManus, B., Polygraph, 28(1):209-22 (1999)] developed by Donald Krapohl, and ASIT Poly Suite [Gordon, N. J., Polygraph, 28(1):209-22 (1999)] developed at the Academy for Scientific Investigative Training. Combined scoring methods are also suitable. In addition, the Integrated Zone Comparison Technique may be employed. [Gordon, N. J., Mohamed, F. B., Faro, S. H., Platek, S. M., Ahmad, H., Williams, J. M., *Physiology & Behavior* 87:251-54 (2006); Gordon, N. J., Fleisher, W. L., Morsie, H., Habib, W., Salah, K., *Polygraph* 29(3):200-25 (1987)].

In some embodiments employing the ASIT Poly Suite "Horizontal Scoring Technique and Academy's Algorithm for Chart Interpretation", each physiological parameter measured by the examiner can be scored based on a degree of reactivity. [See Gordon, N. J., *Polygraph* 28(1):56-64 (1999); Gordon, N. J., *Polygraph* 16(2):116-25 (1987)]. Here, each parameter is placed in a rank order hierarchy. For example, a "6" score may be indicative of the greatest reaction, while a "1" score may be indicative of the least reactivity. Criteria for determining the greatest reaction on rate and depth of respiration (pneumo score) may be based on suppression, apnea and duration of reaction (lack of air). Electrodermal reactions (GSC) can be based on the measurable height of the reaction squared and multiplied by the duration of the subject's reaction. Here, the greatest number of GSC values can receive the greatest score (e.g., "6") and the smallest number can receive the smallest score (e.g., "1"). Similarly, the cardiovascular activity (heart rate) can be ranked according to increases in diastolic blood volumes.

In an embodiment where n parameters are measured, each parameter is weighted evenly (e.g., 1/n for each of n parameters measured). For example in the embodiment above, where both thoracic and abdominal breathing are ranked for determining a single pneumo score, both of the pneumo reactions can be averaged, to maintain a final score that that is based evenly (⅓) for each of the three parameters monitored (e.g., pneumo, cardiovascular rate, and GSC). The ASIT Poly Suite algorithm weighs evenly each parameter, whereas the algorithms from PolyScore and OSS are based on a weighted system heavily favoring the GSC parameter (as described below).

Once each of the parameters for each of the questions are ranked (and pneumo reactions averaged), the sum of three scores (average of the pneumos, plus the GSC and cardio) are representative of the question score. In addition, where comparison questions are used, the comparison question scores may be assigned positive numbers while relevant question scores are assigned negative numbers. Thus, the sum of all of the comparison and relevant question scores represent the examination score.

C. Methods of Measuring and Scoring Behavioral Components.

In some embodiments, one or more behavioral components are measured while the subject responds to questions, including relevant questions. In this respect, the behavioral component(s) can be measured during the subject's response to a relevant question and compared with the subject's response to a control question.

In some embodiments, the subject's responses to be measured may include known truths and known lies. However, it is not necessary that the investigator know prior to questioning a subject that a subject's response to a relevant question is truthful or deceptive.

In preferred embodiments, the behavioral component(s) to be measured include, for example, spoken verbal behavior, non-verbal behavior, and written behavior. These components include voluntary and involuntary behaviors (e.g., natural, subconscious, and instinctual responses to certain stimuli) comprising, for example, foot movement and position; leg movement and position; body movement and alignment; eye contact; eye movement; use of emblems, illustrators, and adaptors; posture and demeanor; restlessness; facial expressions; pupil dilation and constriction; squinting; blinking; eyebrow movement; dry mouth; licking; chewing; swallowing; lip biting; nose touching; facial coloring or whitening; itching; increased heart rate; touching of the eyes, nose or ears; hand positions; arm positions; paralinguistic behaviors; increased vocal pitch; neurolinguistic behavior; unwitting verbal cues; structure of response, both written and oral; written cues; sweating; and breathing rate. Thus, in some embodiments, measuring a behavioral component may include measuring a physiological parameter. Alternative behavioral components, which may be measured and scored in accordance with the present invention, are described in *Effective Interviewing and Interrogation Techniques* $2^{nd}$ *Edition*, Academic Press, Copyright Elsevier, Inc., 2006, Burlington, Mass., which is hereby incorporated by reference herein.

In certain embodiments, a device that provides a graphic record of a subject's behavioral response simultaneously with a physiological response is prescribed. In this embodiment, the polygraph examiner can concentrate on administering the exam instead of trying to observe the subject's movement.

Some behavioral components, such as shifting body movement, arm movement and foot movement may be monitored by devices that are compatible with polygraph devices. These devices are commercially available. For example, the LX4000 computerized polygraph includes accessories such as the Electric Activity Sensor (a pad for a chair having sensors that detect subtle movements as well as gross movements of a subject during a polygraph examination), the Electric Activity Sensor Arm Pads (arm pads having sensors that detect movements of shoulders, forearms and hands of the subject during a polygraph test), Activity Sensor Feet Pads (pads placed on the floor having sensors that detect movements of feet and toes). In some embodiments, a video recorder for recording both audio and visual information may be employed.

In some embodiments, the Forensic Assessment Interview Technique (FAINT) is employed to measure and score a subject's behavior(s). [Gordon, N. J., Fleisher, W. L., *Effective interviewing and interrogation techniques*. San Diego, Calif.: Academic Press (2002)]. FAINT maintains that there are demonstrable differences between a truthful subject's nonverbal, spoken verbal, and written behaviors than those same behaviors in a deceptive suspect, and that these differences can be quantified for accurate deductions. In some embodiments, behavioral components may be measured and scored using the traditional FAINT Three Point Scoring Method. [See Gordon, N. J., Fleisher, W. L., supra].

In other embodiments, the weighted scoring system is preferred. The weighted scoring system is a FAINT analysis technique and can be applied as follows: If the observation correctly agreed with actual outcome 90 percent of the time or better, a number of +3 for truth, or a −3 for deception, representing three standard deviations were assigned. If predictability of the question equaled 80 to 89 percent of final outcome, a +2 for truth, or a −2 for deception, representing two standard deviations were assigned. If predictability of the question equaled 60 to 79 percent of final outcome, a +1 for truth, or a −1 for deception, representing one standard deviation was assigned. If predictability of the question was less than 60 percent of final outcome, a 0 was assigned.

In some embodiments, a subject may be asked to draft a written statement. In these embodiments, the "Scientific Content Analysis" (SCAN) may be performed to assess the subject's truthfulness or deception. [Lesce, Tony, *SCAN: Deception Detection by Scientific Content Analysis*. Law and Order Magazine, Vol. 38, No. 8. (August 1990).]

In some embodiments, the Reid Behavioral Analysis Interview (BAI) method may be conducted. Horvath, Frank; Jayne, Brian and Buckley, Joseph. *Differentiation of Truthful and Deceptive Criminal Suspects in Behavior Analysis Interviews*. Journal of Forensic Sciences, JFSCA, Volume 39, Number 3, pp. 793-807. May, 1994.

These and alternative embodiments for measuring and scoring behavioral components are described in Gordon, N. J., Fleisher, W. L., *Effective Interviewing and Interrogation Techniques*. $2^{nd}$ Edition, Copyright Elsevier, Inc., Academic Press (2006), for example. Devices and methods for measuring and scoring a behavioral component are suitable for use in the present invention. It is expected that new devices and techniques will be developed in the future to measure a behavioral component, and that some will be useful in the methods of the present invention.

D. Methods of Combining the Data Scores of Brain Activation, Physiological Parameters, and Behavioral Components, or Combinations Thereof, to Form a Composite Evaluation Indicative of Truth or Deception.

In some embodiments, the step of combining data scores includes determining a composite score for each of: (A) brain activation in a region or plurality of regions; (B) physiological reactions in a parameter or plurality of parameters; and/or (C) behavioral reactions in a component or a plurality of components and combining the scores for each (e.g., A, B, with C; A with B; A with C; and B with C) to form a composite evaluation indicative of truth or deception in the subject's response to the relevant questions. In some embodiments the steps of monitoring or measuring A, B, or C, and combinations thereof, can be conducted simultaneously. In other embodiments, measurements may be conducted at different times. For example, the subjects may be questioned on three separate occasions (e.g., while being subjected to (A) fMRI analysis, (B) polygraph analysis, and (C) FAINT analysis). It should be noted that in those embodiments that combine use of brain imaging equipment, compatible devices for measuring physiological parameters and/or behavioral components are prescribed.

The order of analysis for each monitoring or measuring device or technique is not essential to the invention. Thus, a subject may be monitored first by FAINT and then by brain imaging and finally by a polygraph; or first by fMRI, then polygraph only; or alternatively, first by polygraph, then FAINT, and finally by fMRI; and so on. Thus, in any of the above embodiments, permutations of the order for employing any of the techniques described herein are acceptable.

The scores obtained for activation, physiological and behavioral monitoring of a given real subject, or any two of these, can be combined, for example, by adding the scores to one another. In this technique, the sum of the scores, or another number directly related to the sum, such as the average of the scores, constitutes the indication of truth or deception for the subject. Desirably, the scores are normalized to a common set of values before adding them. Different weighting factors can be applied to each of the scores in the addition process to emphasize one of the scores in the final indication. Alternatively or additionally, the combining process or normalization process can mathematically emphasize those scores which strongly deviate from the mean. For example, the squares of the scores, rather than the scores themselves, can be added to yield the indication of truthfulness or deception.

In some embodiments, machine learning algorithms or vector machines, which allow training of a machine network with a set of known data (e.g., known brain regions, physiological parameters, and/or behavioral components to be indicative of truth or deception) may be employed. Accordingly, the network may be trained to derive an, indication of truth or deception based upon a test subject's responses to questions/stimuli, which are supplied to the machine for computational analysis. Computational methods and devices for performing the methods of the invention include neural networks, artificial intelligence, and other self-adaptive systems. It should be noted that here, the step of combining the subject's brain response, physiological response, and/or behavioral response data can be integrated with the step of computing a score for each response. Thus, the scoring and combining step can occur in the same operation, such that the ultimate score, which can be indicative of truth or deception, will include a plurality of physiological, behavioral, and brain activation data parameters. In addition, it is expected that new devices and methods (e.g., algorithms) will be developed in the future to combine brain, physiological, and/or behavioral responses, and that some will be useful in the methods of the present invention.

In some aspects of the foregoing discussion and in examples which follow, reference is made to the best-developed brain imaging technology, BOLD fMRI. Any of the above-mentioned technologies, or any other technology capable of functional brain mapping or monitoring brain activation, can be used equivalently in the methods of the invention.

Example 1

Experimental Design

The purpose of these experiments was to assess the ability of the combined polygraph-fMRI methodology to enhance the accuracy of either the polygraph score or an fMRI score alone. Here, multiple physiological parameters were scored and combined with fMRI to determine an accuracy rate for deception (DI-deception indicated) as well as an accuracy rate for non-deceptive individuals (NDI-no deception indicated). Two different polygraph algorithms, ASIT and OSS, were employed in these experiments.

The results using the ASIT polygraph algorithm demonstrated that the combined polygraph-fMRI methodology increased accuracy from 90% (polygraph only) to 100% (combined polygraph and fMRI and increased accuracy from 80% (polygraph only) to 100% (combined fMRI and polygraphy) for the non-deceptive individuals.

Similarly, results using a second independent polygraph algorithm, OSS, demonstrated an increase in accuracy from 72% (polygraph only) to 90% (combined fMRI and polygraphy); an increase in accuracy from 83% (polygraph only) to 100% (combined polygraph and fMRI) for deceptive individuals; and an increase in accuracy from 60% (polygraph only) to 80% (combined polygraph and fMRI) for the non-deceptive individuals.

Materials and Methods fMRI Procedure

The functional MRI experiment used a boxcar type block design for collecting images. The order of the fMRI and polygraph procedure was randomized across subjects. The subjects were instructed to stay still during the scanning. The auditory stimulus was controlled from outside the scanner using Presentation software (NeuroBehavioral Systems) and delivered through headphones that were compatible for use in the MRI environment. Subjects listened to digitally recorded questions read by the investigator who performed the interviews and polygraph tests. The same voice was used across all the subjects and recordings of the questions, which were matched as closely as possible for length, volume, and clarity. All questions were designed to be answered using "Yes" or "No" and subjects were instructed to respond using designated keys on a MR compatible response box (Resonance Technology, Inc). The question format that was used in this study followed a modified positive control polygraph questioning technique. The questions used in the polygraph examinations and the fMRI studies were the same.

Twelve (12) subjects were recruited for this study; however, the data of one subject was eliminated because this subject accepted guilt prior to the start of the study, even though this subject was instructed to lie and try to beat the test. Thus, the experiments were performed in 11 healthy volunteers (five female and six male subjects; mean age, 28.9 years) who were screened for drug use, neurological and neuropsychiatric illness, and contraindications to MR imaging performed with a standard 1.5-T imager (Vision; Siemens, Erlangen, Germany). Ten subjects were right handed, and one was left handed. All subjects underwent an initial preparation phase, an interview phase, a polygraph test, and a functional MR imaging examination. The order of the functional MR imaging examination and the polygraph test was randomized. In the preparation phase, subjects were given the following instructions by one of the investigators:

Scenario 1, guilty subjects: You have been chosen to fire a gun inside the hospital. The only person that will know that you fired the gun is the researcher who gave it to you. After firing the gun, your role in this project is to fool everyone else into believing you did not fire it. The researchers who will interview you and test you via the polygraph and functional MR imaging have been told that you are a suspect in the shooting because someone who looks like you appeared on a video surveillance system in the area around the time of the shooting. Your role is not to be identified as the shooter.

Scenario 2, non-guilty subjects: Someone fired a gun today inside the hospital. The researchers that will interview you and test you via the polygraph and functional MR imaging have been told that you are a suspect in the shooting because someone who looks like you appeared on a video surveillance system in the area around the time of the shooting. Your role is to be cooperative and truthful, since you did not fire the gun. You want to do well in the interview and testing and demonstrate to them you are innocent.

The relevant situation used in this study was a mock shooting, in which a starter pistol with blank bullets was fired. None of the subjects reported having any distress or upset feelings. They were asked to wear goggles for eye protection. This was followed by an interview phase that used the forensic assessment interview technique (FAINT) [Gordon, N. J., Fleisher, W. L., *Effective interviewing and interrogation techniques*. San Diego, Calif.: Academic Press (2002)], in which the subjects were asked about their involvement in the study and basic demographic information was gathered. Functional MR imaging and polygraph testing were performed after the interview.

Of the 11 subjects, five were asked to tell the truth (Scenario 2; i.e., they were not involved in the relevant situation), and six were asked to deliberately lie (Scenario 1; i.e., deny their involvement in the relevant situation). We pooled the subjects who were asked to lie; hereafter, they are referred to as guilty subjects. We also pooled the subjects who were asked to tell the truth; hereafter, they are referred to as non-guilty subjects. The subjects were informed that they would be rewarded $25 for correctly following the instructions. For guilty subjects in the lie-only condition (i.e., subjects were asked to lie to all questions), the relevant question was a subjective lie, since the shooter declared his or her lie with a "yes" response, which was actually the truth. In non-guilty subjects, subjects who told the truth lied to relevant questions, which they declared with a "yes" response and admitted to a crime they did not commit. Similarly, for guilty subjects in the truth-only condition (i.e., subjects were asked to respond truthfully to all questions), the relevant question was a subjective truth, since the shooter declared the truth with a "no" response, which was actually a lie. In non-guilty subjects, the subjective truthful response to relevant questions was "no," since the subjects truthfully denied the act they did not commit.

Initially a high spatial resolution (256*256) T1-weighted spin echo sequence (TR=500 ms; TE=14 ms) was used to acquire anatomical images. Twenty-five (25) contiguous axial images were positioned and aligned parallel to the AC-PC (anterior commissure and posterior commissure respectively) line covering the entire brain (Talairach, J., Tournoux, P., *Co-planar stereotaxic atlas of the human brain: 3-dimensionsal proportional system-an approach to cerebral map-*

*ping*. New York, N.Y.: Thieme, 1998). Later, functional images were acquired with echo planar (EPI-FID) sequence in the same plane as the structural images. The imaging parameters were: matrix size=128*128; field of view (FoV) =22 cm; slice thickness=5 mm; TR=4s; TE=54 ms; and NEX=1. The in-plane image resolution was 1.72×1.72×5.00 mm.

Figure 2:
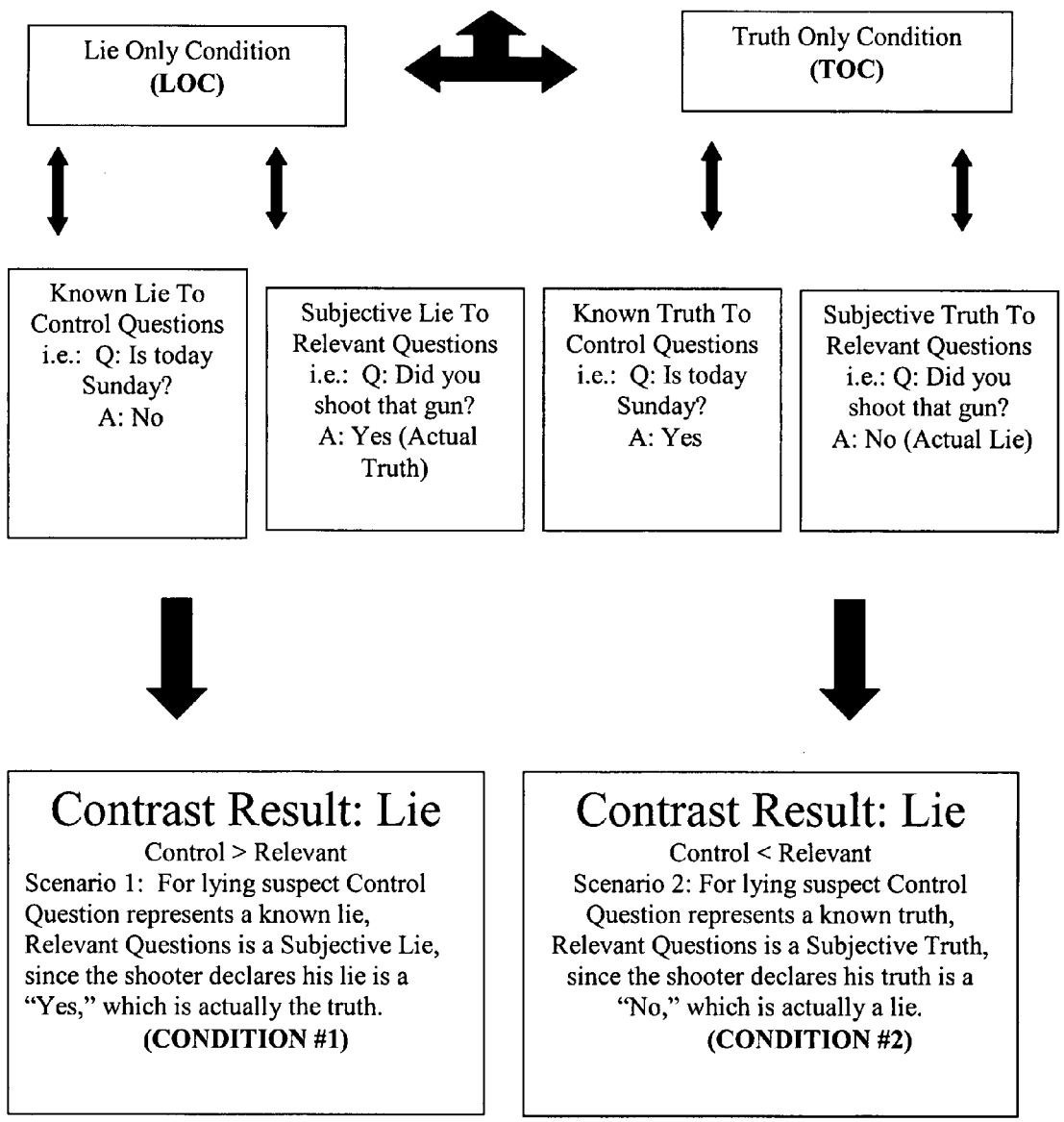
FIG. 2 depicts a diagram illustrating the questioning strategy as performed on guilty subjects (GS).
Figure 3:
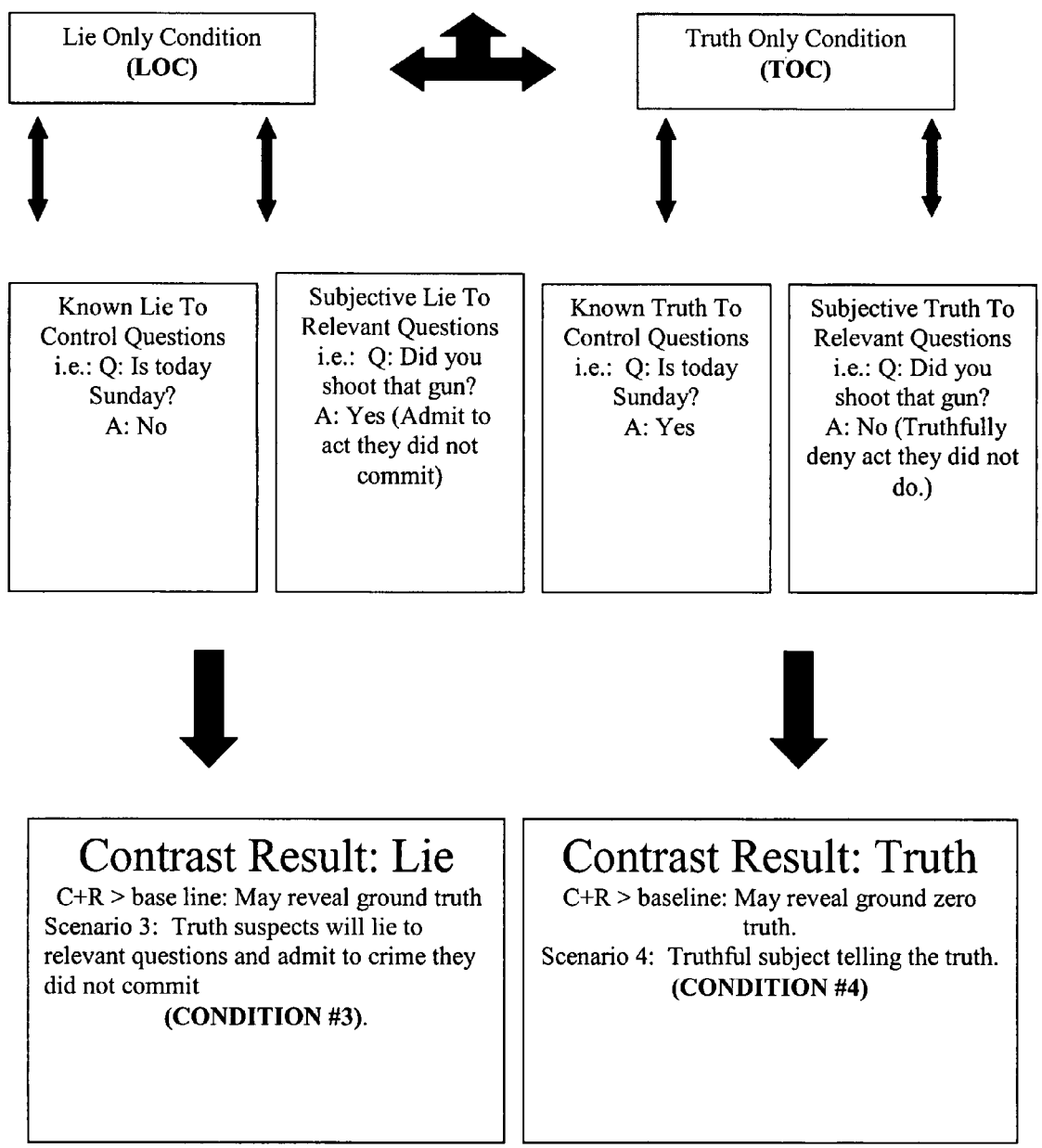
FIG. 3 depicts a diagram illustrating the questioning strategy as performed on non-guilty subjects (NGS).

The subjects were presented with 5 blocks (control questions), 5 blocks (rest), 5 blocks (relevant questions), 5 blocks (rest), for a total of 20 blocks and 120 volumes. During each block (24 sec long), 6 volumes of echo-planar images (EPI) were acquired, yielding a total of 120 EPI volumes. It was expected that the subjects denying their involvement in the relevant situation would produce a greater autonomic response to the relevant questions than to control questions (FIGS. 2 and 3). Continuous scanning was performed until all the 20 blocks were completed.

Two separate fMRI experiments were conducted. The first session named "Lie Only Condition" (LOC) was carried out to compare the brain activity during "known lie" to control questions and subjective lie to relevant questions. This was followed by another session named "Truth Only Condition" (TOC) where the brain activity during "known truth" to control questions and subjective truth to relevant questions were compared. The questions were randomized and repeated between different blocks. The instructions pertaining to the LOC, where the subjects were asked to lie to all the questions and the instructions pertaining to TOC where the subjects were asked to tell the truth to all the questions were given while the subjects were inside the scanner and prior to the specific experimental condition. At the end of the study all the subjects were debriefed about the study and their participation by two investigators.

Polygraph Procedure

A certified polygraph examiner and an investigator in this study with 26 years of investigative, administrative and polygraph experience performed the interviews and polygraph measurements on all the subjects. The physiological responses from the healthy subjects were measured by using a four-channel computerized LX-4000 polygraph instrument. Three different types of physiological responses were measured. The rate and the depth of respiration were measured by two different pneumographs secured around the chest and the abdomen (pneumo). A blood pressure cuff placed around the bicep of the subject was used to measure cardiovascular activity (cardio). The galvanic skin conductance (GSC), a measure of electrical conductivity related to perspiration, was measured with electrodes attached to the index and forefinger of the volunteers. All the polygraph signals were digitally recorded and the responses were displayed on a moving chart of a laptop computer using the software provided by the Lafayette Instrument Company, Lafayette, Ind. The polygraph results were analyzed using two different polygraph scoring methodologies: Objective Scoring System (OSS) [Krapohl, D., McManus, B., Polygraph, 28(1):209-22 (1999)] developed by Donald Krapohl and ASIT Poly Suite [Gordon, N. J., Polygraph, 28(1):209-22 (1999)] developed at the Academy for Scientific Investigative Training.

fMRI Statistical Analysis

The post-acquisition preprocessing and statistical analysis was performed using SPM2 (Statistical Parametric Mapping, Version 2, Wellcome Department of Cognitive Neurology, University College of London, London, United Kingdom run under the Matlab® (The Mathworks, Inc., Natick, Mass.) environment by two of the investigators. Images were converted from the Siemens format into the ANALYZE (AnalyzeDirect, Inc., Lenexa, Ky.) format adopted in the SPM package. A 3-D automated image registration routine (six-parameter rigid body, sinc interpolation; second order adjustment for movement) was applied to the volumes to realign them with the first volume of the first series used as a spatial reference. All functional and anatomical volumes were then transformed into the standard anatomical space using the T2 EPI template and the SPM normalization procedure. This procedure uses a sinc interpolation algorithm to account for brain size and position with a 12 parameter affine transformation, followed by a series of non-linear basic function transformations seven, eight, and seven nonlinear basis functions for the x, y, and z directions, respectively, with 12 nonlinear iterations to correct for morphological differences between the template and given brain volume. Next, all volumes underwent spatial smoothing by convolution with a Gaussian kernel of 8 cubic mm full width at half maximum, to increase the signal-to-noise ratio (SNR) and account for residual intersession differences.

Subject-level statistical analyses were performed using the general linear model in SPM2 (Statistical Parametric Mapping, Version 2, Wellcome Department of Cognitive Neurology, University College of London, London, United Kingdom). The scans corresponding to the relevant and control conditions in the two trials [LOC (lie-only condition) & TOC (truth-only condition)] in the two groups of subjects GS (guilty subjects) and NGS (non-guilty subjects) [GS=subjects instructed to lie on the relevant questions and NGS=subjects instructed to tell the truth on the relevant questions] were modeled using a canonical hemodynamic response function. Contrast maps were obtained with the following linear contrasts of event types: relevant vs. control (GS, LOC: Lie effect), control vs. relevant (GS, TOC: Lie effect), (relevant+control) vs. baseline (NGS, LOC: Lie effect), (relevant+control) vs. baseline (NGS, TOC: Truth effect).

Next, group-level random-effects analyses for main effects were performed by entering whole brain contrasts into one-sample t-tests. A significance threshold based on spatial extent using a height of t≥3.00 and cluster probability of an uncorrected p≤0.001 was applied to the effects of interest and surviving voxels were retained for further analyses (spatial extent threshold >10 voxels). Statistical parametric maps (SPM {t}) were generated to show visual representation of the areas in the brain wherein statistically significant differences between BOLD (Blood Oxygen Level Dependent) contrast during truth-telling and deception conditions are present. The analysis scheme that was performed in this study and sample questions are shown in FIGS. 2 and 3.

Polygraph Analysis

All the polygraph charts were interpreted using ASIT Poly Suite and the Objective Scoring System (OSS).

Utilizing the ASIT Poly Suite "Horizontal Scoring Technique and Academy's Algorithm for Chart Interpretation" [See Gordon, N. J., Mohamed, F. B., Faro, S. H., Platek, S. M., Ahmad, H., Williams, J. M., *Physiology & Behavior* 87:251-54 (2006)] each physiological parameter monitored by the examiner was placed in a rank order hierarchy according to a quantified degree of reactivity from greatest reaction receiving a "6" to the least reaction receiving a "1". Criteria for determining the greatest reaction in the pneumo was based on suppression, apnea and duration of reaction (lack of air). The electro-dermal reactions, GSC, were ranked based on the height of the reaction squared multiplied by the duration of the reaction. The greatest number received the highest rank. The cardio reactions were ranked based on diastolic blood volume and blood pressure increases. The question format is described in FIG. 7.

Since both thoracic and abdominal breathing were ranked, these two parameter scores for each question were then averaged, to maintain a final decision which would be based evenly (⅓) for each of the three parameters monitored. This component input differs from that of the other two algorithms, which make decisions based on a weighted system heavily favoring electro-dermal activity.

Once each question's parameters were ranked, and the pneumo reactions were averaged, the sum of the three scores (average of the pneumos, plus the GSC and cardio) represented the question score. Comparison question scores were given positive numbers and relevant question scores received negative numbers. The sum of all of the comparison and relevant scores represented the examination score. If the examination score was a +13 or higher the examinee was determined to be truthful when they denied shooting the gun. If the score was a −13 or lower, they were determined to be deceptive. Any score between the + or −13 was determined to be inconclusive.

The Objective Scoring System (OSS) was introduced by Donald Krapohl and Barry McManus in 1999 and utilized measurements of criteria established by Raskin et al. in 1988: Time line length of the pneumo (lack of air equals reaction) which is measured for 10 sec after question onset, electro-dermal amplitude and blood volume increases. The physiological parameters are weighted similar to PolyScore®, with 50% of the decision generated from electro-dermal activity, 25% from respiration and 25% from blood volume. This system utilizes a traditional 7 point scale, where scores of a +6 or higher are interpreted as truthful, −6 and lower are deceptive, and scores in between are deemed inconclusive.

Combined fMRI and Polygraph Analysis

Initially group analysis of the fMRI data based on conditions number 2 and 4 from FIGS. 2 and 3 were used to calculate the regions of the brain involved. Condition #2 showed us deceptive patterns of the brain (for lying subject Control Question represents a known truth, Relevant Question is a Subjective Truth, since the shooter declares his truth is a "No," which is actually a lie, FIG. 2). Condition #4 showed us the truthful patterns of the brain activation (Truthful subject telling the truth, FIG. 3). FIGS. 4A and 4B list the overall regions involved that were activated during these conditions.

Based on the proportion of the subjects (deceptive subjects and truthful subjects) a percentage score was assigned to each area that was activated in the deceptive and truthful conditions.

A percentage difference score with sign (positive or negative) was assigned between the deceptive and truthful conditions for each individual area. A positive sign was assigned if there were more truthful subjects who activate that particular area of the brain and a negative sign was assigned if more deceptive subjects activate a particular region of the brain.

The percentage difference scores for individual areas were then normalized and assigned a value ranging between +/−27 in accordance with the polygraph scoring technique to establish an fMRI score for each area of brain activated.

Next, single subject analysis of the fMRI data based on conditions number 2 and 4 were used to calculate the regions of the brain that were involved in individual subjects. Condition #2 showed us deceptive patterns of the brain and condition #4 showed us the truthful patterns of the brain activation. Subjects showing activation of brain areas were assigned with the fMRI scores pertaining to that individual area derived from the group analysis. The grand total fMRI score was obtained by summing the individual fMRI scores of each subject.

FMRI score and polygraph score on individual subjects were averaged to establish an overall score. The range of cutoff was established between +/−18.

Results

The foregoing combined scoring technique was tested on two polygraph algorithms-ASIT and OSS. The result of combining the fMRI score with the polygraph score using the ASIT algorithm is shown in FIG. 5. The results reveal that overall (1) the combined polygraph-fMRI methodology demonstrated an increase in accuracy from 90% (polygraph only) to 100% (combined polygraph and fMRI), and that (2) the combined polygraph-fMRI methodology demonstrated an increase in accuracy from 80% (polygraph only) to 100% (combined polygraph and fMRI) for the non-deceptive individuals. In FIG. 5 a bolded word represents increased sensitivity.

The results of combining the fMRI score with the polygraph score using a second independent polygraph algorithm (OSS) is shown in FIG. 6. The results reveal that overall (1) the combined polygraph-fMRI methodology demonstrated an increase in accuracy from 72% to 90%, and that (2) the combined polygraph-fMRI methodology demonstrated an increase in accuracy from 83% (polygraph only) to 100% (combined polygraph and fMRI) for the deceptive individuals, and that (3) the combined polygraph-fMRI methodology demonstrated an increase in accuracy from 60% (polygraph only) to 80% (combined polygraph and fMRI) for the non-deceptive individuals. In FIG. 6 a bolded word represents increased sensitivity.

The publications cited in the specification are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of deriving an indication of truth or deception comprising the steps of:
   (a) monitoring activation of a plurality of regions of a subject's brain by applying functional magnetic resonance imaging (fMRI) while the subject responds to questions including relevant questions to determine an fMRI indicium of response for each such region;
   (b) measuring a plurality of physiological parameters of the subject including respiratory volume, at least one cardiac parameter related to change in heart rate, and galvanic skin response ("GSR") while the subject responds to questions including relevant questions and deriving a score for each physiological parameter based on such measurements; and
   (c) combining the results of steps (a) and (b) by:
      (i) calculating a composite activation score based on the degrees of activation of all of said plurality of regions, by applying a weighting factor to the fMRI indicium of response for each of said regions of the brain, the weighting factor for each region being related to a probability that activation of such region indicates deception; and
      (ii) combining such composite with the scores for all of the physiological parameters to form a further score indicative of truth or deception in the subject's response to the relevant questions.

2. A method as claimed in 1 further comprising the step of monitoring a response of the subject's brain while the subject responds to a series of control questions, wherein said step of monitoring activation of a plurality of regions of the subject's brain while the subject responds to relevant questions includes comparing an indicium of activity for each of said regions during response to the relevant questions with the same indicium during response to control questions.

3. A method as claimed in 2 wherein said indicium of activity is a binary indicator having a first value indicative of activation and a second value indicative of inactivation.

4. A method as claimed in 2 wherein said indicium of activity is a degree of activation or inactivation each represented by a real number value.

5. A method as claimed in 2 wherein the subject's response to said control questions includes known lies and known truths.

6. A method as claimed in claim 1 wherein, for each region in a first set of regions of the brain, activation of which is associated with lying, said weighting factors have a first sign and for each region in a second set of regions of the brain, activation of which is associated with truthfulness, said weighting factors have a second sign opposite to said first sign.

7. A method as claimed in claim 1 wherein, for each region, the step of applying a weighting factor includes multiplying an indicium of activation by the factor for such region.

8. A method as claimed in claim 1 further comprising the step of determining said factors by monitoring activation of a plurality of regions of the brains of a plurality of subjects while the subjects respond to control questions.

9. A method as claimed in claim 1 wherein said at least one cardiac parameter is selected from the group consisting of heart rate, blood pressure, and blood volume.

10. A method as in claim 1 wherein said step of measuring physiological parameters includes the step of measuring a change in at least one said parameter.

11. A method as in claim 1 wherein the step of deriving a score for each physiological parameter includes the step of quantifying a degree of reactivity in response to questions including relevant questions, said degree of reactivity being represented by a real number.

12. A method as claimed in claim 1 wherein said combining step includes a step of calculating a composite physiological score by applying at least one algorithm selected from the group consisting of PolyScore, OSS, ASIT Poly Suite and combinations thereof, and combining the activation score with the physiological score.

13. A method as claimed in claim 1 wherein said step of monitoring activation of a plurality of regions of a subject's brain and said step of measuring said physiological parameters while the subject responds to questions are conducted simultaneously.

14. A method as claimed in claim 1 wherein said step of monitoring activation of a plurality of regions of a subject's brain and said step of measuring said physiological parameters while the subject responds to questions are conducted at different times.

15. A method as claimed in claim 1 further comprising the step of:
(a) measuring one or more behavioral components while the subject responds to said questions including the relevant questions; and
(b) combining the results of step (a) with said further score to form an evaluation indicative of truth or deception in the subject's response to the relevant questions.

16. A method as claimed in claim 15 wherein said step of measuring one or more behavioral components includes measuring one or more components selected from the group consisting of spoken verbal behavior, non-verbal behavior, and written behavior.

17. A method as claimed in 15 wherein said step of measuring one or more behavioral components includes using a Forensic Assessment Interview Technique (FAINT) analysis technique.

18. A method as claimed in claim 15 wherein said step of measuring one or more behavioral components includes measuring a plurality of behavioral components.

19. A method as claimed in claim 1 wherein, in said step of combining the activation score with the scores for all of the physiological parameters, the scores for the cardiac parameter, the respiratory parameter and GSR are weighted equally with one another.

20. A method as claimed in claim 1 wherein said step of combining the activation score with the scores for all of the physiological parameters is performed by calculating a physiological score based on the scores for all of the physiological parameters and then combining the activation score with the physiological score.

* * * * *